United States Patent
Gottscho

(10) Patent No.: US 10,041,868 B2
(45) Date of Patent: Aug. 7, 2018

(54) ESTIMATION OF LIFETIME REMAINING FOR A CONSUMABLE-PART IN A SEMICONDUCTOR MANUFACTURING CHAMBER

(71) Applicant: Lam Research Corporation, Fremont, CA (US)

(72) Inventor: Richard Alan Gottscho, Pleasanton, CA (US)

(73) Assignee: Lam Research Corporation, Fremont, CA (US)

( * ) Notice: Subject to any disclaimer, the term of this patent is extended or adjusted under 35 U.S.C. 154(b) by 219 days.

(21) Appl. No.: 14/961,756

(22) Filed: Dec. 7, 2015

(65) Prior Publication Data

US 2016/0216185 A1 Jul. 28, 2016

Related U.S. Application Data

(60) Provisional application No. 62/109,016, filed on Jan. 28, 2015.

(51) Int. Cl.
*G01N 3/56* (2006.01)
*H01J 37/32* (2006.01)
(Continued)

(52) U.S. Cl.
CPC .............. *G01N 3/56* (2013.01); *C23C 16/50* (2013.01); *C23C 16/52* (2013.01);
(Continued)

(58) Field of Classification Search
CPC ..... G01N 3/56; C23C 16/52; H01J 37/32009; H01J 37/32935; H01J 37/3299
See application file for complete search history.

(56) References Cited

U.S. PATENT DOCUMENTS 4,545,882 A * 10/1985 McKelvey .......... C23C 14/3407
204/192.13
2004/0125360 A1 7/2004 Ludviksson et al.
(Continued)

FOREIGN PATENT DOCUMENTS

GB 2 199 340 A 7/1988

OTHER PUBLICATIONS

European Search Report, Application No. EP 16 152 692.6, dated Jun. 20, 2016.

*Primary Examiner* — Lisa Caputo
*Assistant Examiner* — David Z Huang
(74) *Attorney, Agent, or Firm* — Martine Penilla Group, LLP

(57) ABSTRACT

A consumable part, for use inside a chamber where plasma is used to process a semiconductor substrate, includes a body and a trigger feature. The body has a surface configured to be exposed to the plasma during processing in the chamber, and the trigger feature is integrated within the body. The trigger feature includes a void disposed under the surface of the body, where the void is configured to become visible when the surface is eroded from exposure to the plasma over time. The void becoming visible is an identifiable feature on the surface of the body that indicates a wear level for the consumable part, the wear level being associated with an amount of processing time remaining for the consumable part.

20 Claims, 12 Drawing Sheets

(51) Int. Cl.
*C23C 16/50* (2006.01)
*C23C 16/52* (2006.01)
*H01L 21/67* (2006.01)

(52) U.S. Cl.
CPC .... *H01J 37/32009* (2013.01); *H01J 37/3244* (2013.01); *H01J 37/3299* (2013.01); *H01J 37/32935* (2013.01); *H01L 21/67069* (2013.01); *H01L 21/67253* (2013.01)

(56) References Cited

U.S. PATENT DOCUMENTS

2005/0171730 A1   8/2005   Mitrovic et al.
2010/0046156 A1*  2/2010   Wei .................. A45C 11/18
                                              361/679.32

\* cited by examiner

The hole depth may be a measure of the life left in the edge ring

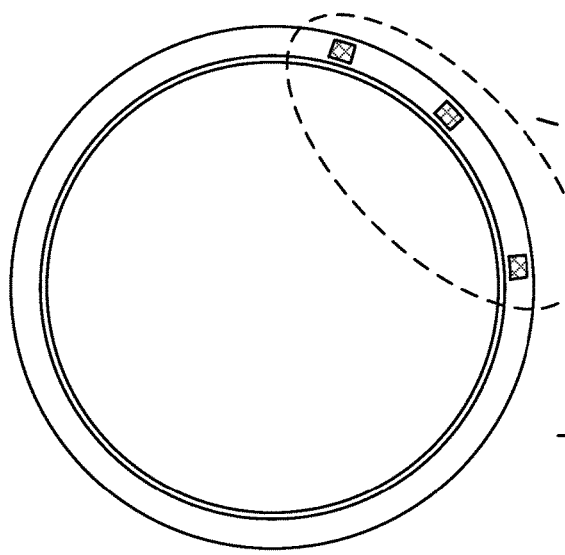
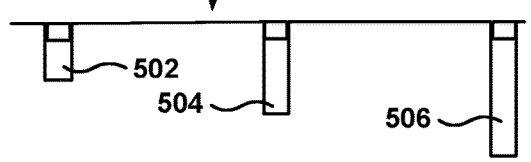
Fig. 5A  Fig. 5B
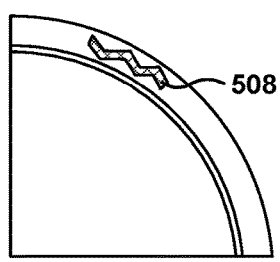
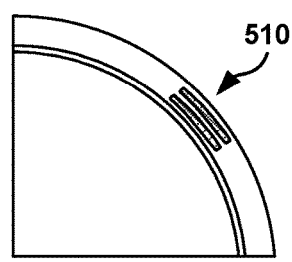
Fig. 5C  Fig. 5D
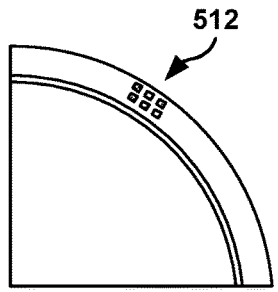
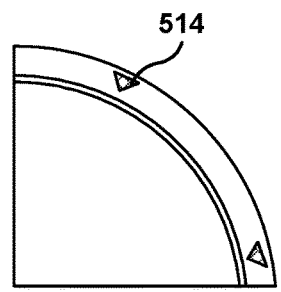
Fig. 5E  Fig. 5F

ESTIMATION OF LIFETIME REMAINING FOR A CONSUMABLE-PART IN A SEMICONDUCTOR MANUFACTURING CHAMBER

CLAIM OF PRIORITY

This application claims priority from U.S. Provisional Patent Application No. 62/109,016, filed Jan. 28, 2015, and entitled "ESTIMATION OF LIFETIME REMAINING FOR A CONSUMABLE-PART IN A SEMICONDUCTOR MANUFACTURING CHAMBER." This provisional application is herein incorporated by reference.

BACKGROUND

1. Field of the Invention

The present embodiments relate to methods for improving semiconductor process uniformity, and more particularly, methods, systems, and computer programs for generating system notifications regarding the lifetime remaining for consumable parts in a semiconductor processing chamber.

2. Description of the Related Art

Plasma has long been employed to process substrates (e.g., wafers or flat panels) to form electronic products (e.g., integrated circuits or flat panel displays). Semiconductor wafers are typically placed in an etch chamber with a photoresist mask layer to direct the etch of the underlying materials. The etching process removes the underlying materials not covered by the photoresist.

The etch process may also remove material from the surfaces of parts within the plasma chamber. Over time, the parts inside the processing chamber may be damaged or altered due to the exposure to the plasma and the etching process.

In a chamber where one or more parts are defective, process efficiency can be substantially reduced, resulting in costly expenses to diagnose and solve problems. Sometimes, parts are kept in the chamber beyond the expected lifetime of the parts because the system administrator is not aware that a particular consumable part should be replaced.

It is in this context that embodiments arise.

SUMMARY

Methods, devices, systems, and computer programs are presented for predicting the remaining lifetime of a consumable part in semiconductor manufacturing equipment. It should be appreciated that the present embodiments can be implemented in numerous ways, such as a method, an apparatus, a system, a device, or a computer program on a computer readable medium. Several embodiments are described below.

What is desired is a system that automatically assesses the lifetime of consumable parts in the chamber, and determines when parts should be replaced, in order to operate with high efficiency a semiconductor processing system.

In one embodiment, a consumable part, for use inside a chamber where plasma is used to process a semiconductor substrate, is presented. The consumable part includes a body and a trigger feature. The body has a surface configured to be exposed to the plasma during processing in the chamber. The trigger feature is integrated within the body and includes a void disposed under the surface of the body. The void is configured to become visible when the surface is eroded from exposure to the plasma over time. The void becoming visible is an identifiable feature on the surface of the body that indicates a wear level for the consumable part, the wear level being associated with an amount of processing time remaining for the consumable part.

In another embodiment, a system is presented. The system includes a chamber, a consumable part, an inspection scope, and the controller. The chamber is configured for generating plasma used to process a semiconductor substrate. The consumable part is configured to be used inside the chamber, the consumable part including a body and a trigger feature. The body has a surface configured to be exposed to the plasma during processing in the chamber, and the trigger feature is integrated within the body. The trigger feature includes a void that is disposed under the surface of the body, and the void is configured to become visible when the surface is eroded from exposure to the plasma over time. Further, the inspection scope is configured for inspecting the consumable part while the consumable part is in the chamber. The controller is configured to determine if the void is visible based on information obtained by the inspection scope, the void becoming visible being an identifiable feature on the surface of the body that indicates a wear level for the consumable part, the wear level being associated with an amount of processing time remaining for the consumable part.

In yet another embodiment, a method for detecting wear on a consumable part is presented. The method includes an operation for placing the consumable part in a chamber for semiconductor manufacturing, where the consumable part includes a body and a trigger feature, the body having a surface configured to be exposed to plasma during processing in the chamber, the trigger feature integrated within the body. The trigger feature includes a void that is disposed under the surface of the body, where the void is configured to become visible when the surface is eroded from exposure to the plasma over time, the void becoming visible being an identifiable feature on the surface of the body that indicates a wear level for the consumable part. The method further includes operations for inserting an inspection scope in the chamber, and for analyzing information obtained by the inspection scope to determine if the void is visible. The method further includes an operation for determining the amount of time left before replacing the consumable part in the chamber when the void becomes visible.

Embodiments presented herein provide methods, systems, and computer programs for predicting time for wet clean, resulting in increased manufacturing predictability, while downtime is minimized. By managing consumable-part lifetime, the cost of the consumable parts is minimized while the operation of the chamber is improved. Other aspects will become apparent from the following detailed description, taken in conjunction with the accompanying drawings.

BRIEF DESCRIPTION OF THE DRAWINGS

The embodiments may best be understood by reference to the following description taken in conjunction with the accompanying drawings.

FIGS. 5A-5B illustrate a trigger feature having three holes of different lengths, according to one embodiment.

FIGS. 5C-5F illustrate the top views of trigger features with different configurations, according to several embodiments.

DETAILED DESCRIPTION

The following embodiments describe methods, devices, systems, and computer programs for generating system notifications regarding the lifetime remaining for consumable parts in a semiconductor processing chamber.

A trigger feature is embedded into the surface of a consumable part to assess the lifetime remaining of the part, such as an edge ring in a semiconductor chamber. In one implementation, the trigger feature includes a capping element above a space embedded into the edge ring. The capping element is coplanar with the edge ring, and as the top surface of the edge ring gets eroded due to etching on the chamber, the capping element is also eroded. After a certain amount of erosion, the capping element is completely worn off and the space underneath the capping element is exposed on the top surface of the edge ring. Visual inspection can then be used to analyze the surface of the edge ring and determine if the trigger feature is visible. Once the trigger feature is visible, a predetermined amount of lifetime is left before replacing the consumable part.

It will be apparent, that the present embodiments may be practiced without some or all of these specific details. In other instances, well-known process operations have not been described in detail in order not to unnecessarily obscure the present embodiments.

Figure 1A:
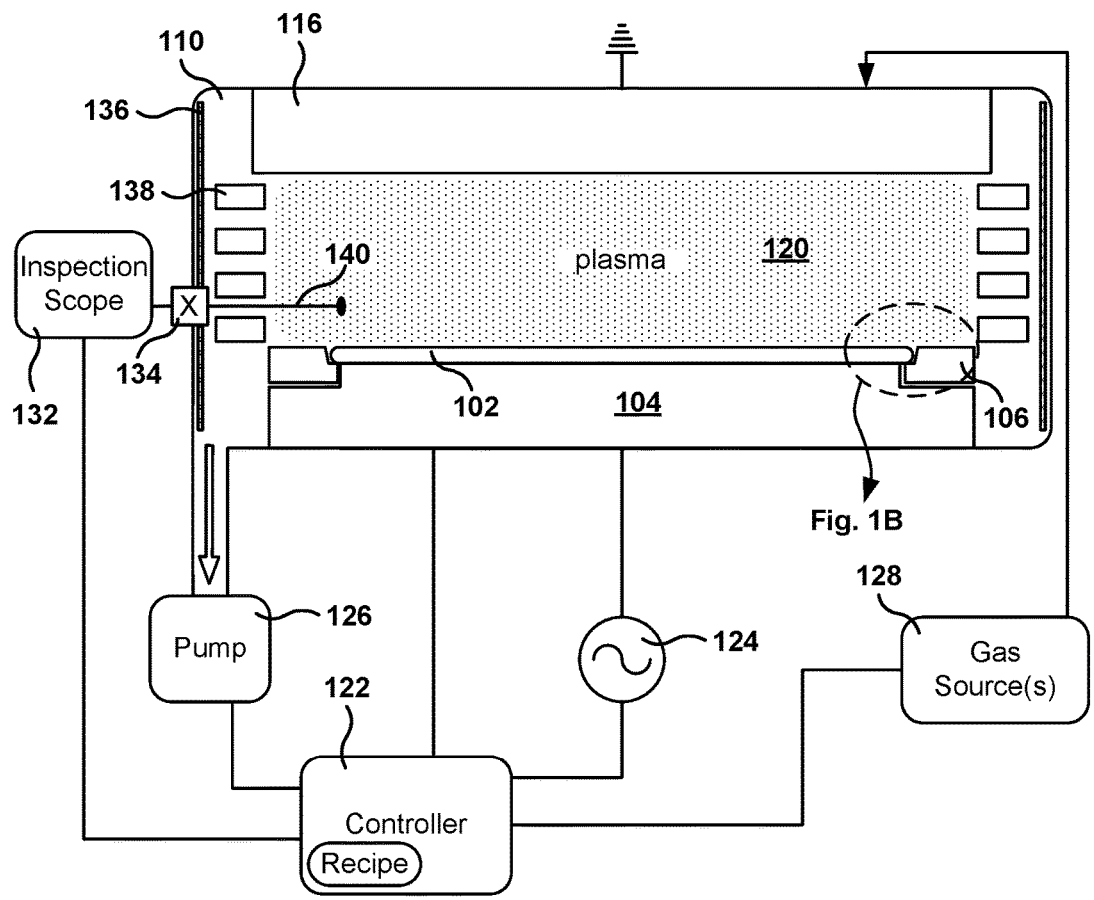
FIG. 1A is a capacitive coupled plasma processing system, according to one embodiment.

FIG. 1A is a capacitive coupled plasma processing system, according to one embodiment. The capacitive coupled plasma processing system includes a plasma process chamber 110, and controller 122, radiofrequency (RF) source 124, pump 126 and one or more gas sources 128 are coupled to the plasma process chamber 110. In some embodiments, the chamber may have one or more RF sources coupled to the top electrode. The plasma process chamber 110 includes an electrostatic chuck 104 for supporting a wafer 102 to be processed, and an edge ring 106. In some embodiments, the plasma process chamber 110 may also include confinement rings for confining the plasma in the chamber, and a chamber wall cover 136.

In some embodiments, plasma process chamber 110 may include an inspection scope 132 (e.g., a borescope), which includes an optical extension 140 that is operable to enter the inside the chamber through valve 134 to inspect one or more parts within the chamber. Any inspection scope may be used, as long as the inspection scope is able to detect the trigger feature. In some embodiments, the inspection scope may be one of a optical camera, imaging camera, SIMs (Scanning Electron Microscopes), RGB cameras, infrared cameras, depth sensing cameras, or any other camera that can detect color or difference in reflections.

Some of the parts inside the chamber are consumable parts, which, due to the impact of etching or other processes in the chamber, have to be replaced after a certain number of hours of operation because of the degradation of the parts. For example, edge ring 106, confinement rings 138, chamber wall cover 136, are examples of consumable parts, but other chambers may include additional parts that are also consumable and need to be replaced over time.

RF source 124 can include multiple RF sources or a single RF source capable of producing multiple frequencies of the RF signals from between about 100 kHz to about 300 MHz. By way of example, some RF signals have frequencies of about 27 MHz to about 60 MHz. The RF signals can have an RF power of between about 50 w and about 10 kw. By way of example, between about 100 w and about 1500 w. The RF source 124 can produce pulsed or non-pulsed RF signals.

The controller 122 includes a processor, memory, software logic, hardware logic and input and output subsystems from communicating with, monitoring and controlling the capacitive coupled plasma processing system 100. The controller 122 also includes one or more recipes including multiple set points various operating parameters (e.g., voltage, current, frequency, pressure, flow rate, power, temperature, etc.) for operating the capacitive coupled plasma processing system.

The plasma process chamber 110 also includes an upper electrode 116. In operation, the upper electrode 116 is typically grounded but could be biased or coupled to a second RF source (not shown). The RF source 124 provides an RF signal to the electrostatic chuck 104 and the gas sources 128 inject the desired process gas(es) into the chamber 110. A plasma 120 is then formed between the upper electrode 116 and the electrostatic chuck 104. The plasma 120 can be used to etch the surface of the wafer 102 or volatilize deposits formed on various inner surfaces of the plasma process chamber 110.

In some implementations, a controller is part of a system, which may be part of the above-described examples. Such systems can comprise semiconductor processing equipment, including a processing tool or tools, chamber or chambers, a platform or platforms for processing, and/or specific processing components (a wafer pedestal, a gas flow system, etc.). These systems may be integrated with electronics for controlling their operation before, during, and after processing of a semiconductor wafer or substrate. The electronics may be referred to as the "controller," which may control various components or subparts of the system or systems. The controller, depending on the processing requirements and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, wafer transfers into and out of a tool and other transfer tools and/or load locks connected to or interfaced with a specific system.

Broadly speaking, the controller may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor wafer or to a system. The operational parameters may, in some embodiments, be part of a recipe defined by process engineers to accomplish one or more processing steps during the fabrication of one or more layers, materials, metals, oxides, silicon, silicon dioxide, surfaces, circuits, and/or dies of a wafer.

The controller, in some implementations, may be a part of or coupled to a computer that is integrated with, coupled to the system, otherwise networked to the system, or a combination thereof. For example, the controller may be in the "cloud" or all or a part of a fab host computer system, which can allow for remote access of the wafer processing. The computer may enable remote access to the system to monitor current progress of fabrication operations, examine a history of past fabrication operations, examine trends or performance metrics from a plurality of fabrication operations, to change parameters of current processing, to set processing steps to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

Without limitation, example systems may include a plasma etch chamber or module, a deposition chamber or module, a spin-rinse chamber or module, a metal plating chamber or module, a clean chamber or module, a bevel edge etch chamber or module, a physical vapor deposition (PVD) chamber or module, a chemical vapor deposition (CVD) chamber or module, an atomic layer deposition (ALD) chamber or module, an atomic layer etch (ALE) chamber or module, an ion implantation chamber or module, a track chamber or module, and any other semiconductor processing systems that may be associated or used in the fabrication and/or manufacturing of semiconductor wafers.

As noted above, depending on the process step or steps to be performed by the tool, the controller might communicate with one or more of other tool circuits or modules, other tool components, cluster tools, other tool interfaces, adjacent tools, neighboring tools, tools located throughout a factory, a main computer, another controller, or tools used in material transport that bring containers of wafers to and from tool locations and/or load ports in a semiconductor manufacturing factory.

Figure 1B:
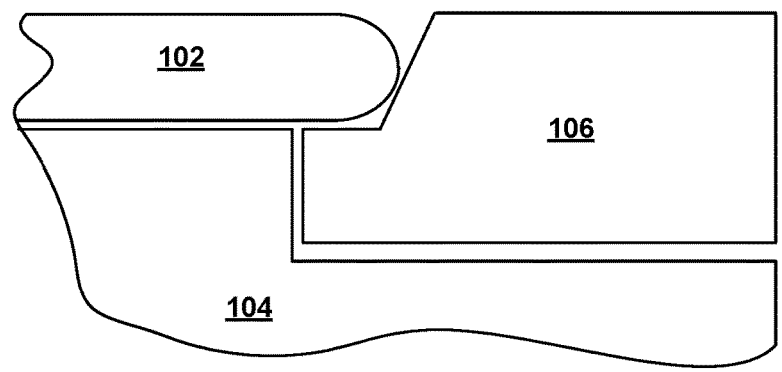
FIG. 1B is a detailed side view of an edge portion of the wafer, according to one embodiment.

FIG. 1B is a detailed side view of an edge portion of the wafer, according to one embodiment. Edge ring 106 surrounds the electrostatic chuck 104. In one embodiment, a portion of the surface of the edge ring 106 extends under the edge of the wafer 102, but in other embodiments, the edge ring 106 may sit next to the wafer 102 without supporting wafer 102. Because wafer 102 is supported by the electrostatic chuck 104, the RF power is driven through the electrostatic chuck and into the wafer.

During the etch process, etch byproducts deposit on the inner surfaces of the plasma process chamber 110. The etch byproducts can include polymeric residue, titanium and other metallic compounds and silicon compounds. The etch byproducts may deposit on any surface within the plasma processing chamber 110 where the plasma 120 disassociated process gas species may diffuse to, including spaces and other inner surfaces of plasma process chamber. Additionally, over time some of the parts of the chamber may be eroded (e.g., reducing the thickness of the edge ring 106) due to the etch process.

Figure 2A:
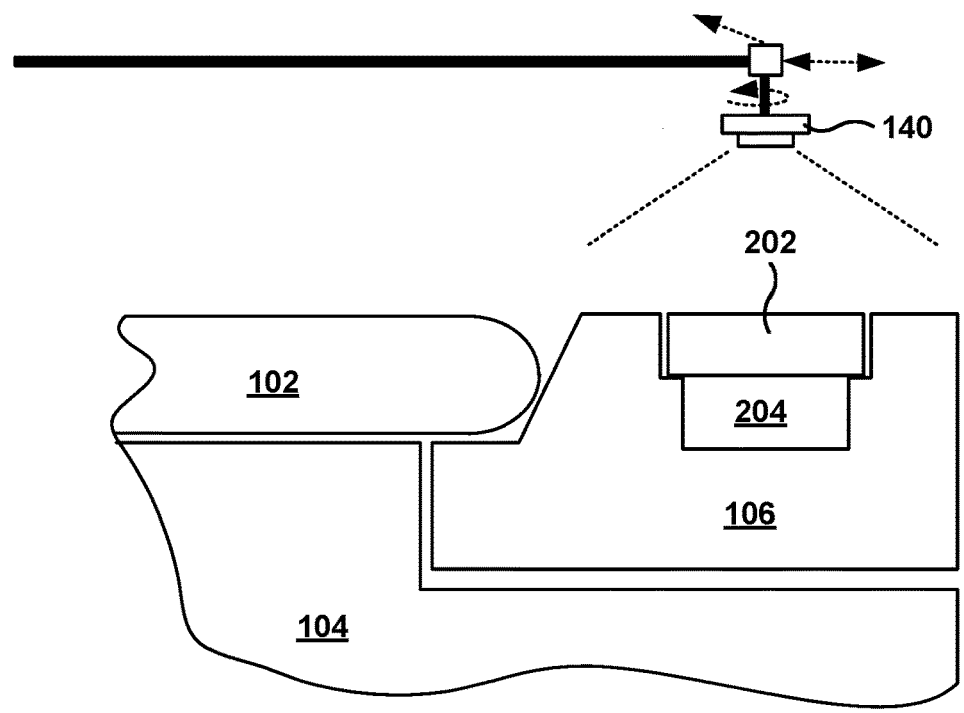
FIG. 2A is a detailed side view of an edge ring with a trigger device for detecting wear on the edge ring, according to one embodiment.

FIG. 2A is a detailed side view of an edge ring with a trigger device for detecting wear on the edge ring, according to one embodiment. Embodiments presented herein, include a trigger feature in the edge ring to assist in determining when the edge ring is deteriorating, for example, by determining the lifetime left in the edge ring or by determining that the edge ring should be replaced immediately or that a maintenance process must be performed.

The edge ring 106 of FIG. 2A has been modified to include a trigger feature. In one embodiment, the trigger feature includes a capping element 202, also referred to as trigger cap or simply cap, and a micro-chamber 204, which is a space, also referred to as a hole, recess, cavity or void, in the consumable part (e.g., edge ring) covered by capping element 202. The void is an intentional element defined in the edge ring 106. In some embodiments, the void is buried within the body of the edge ring. Further, the void may be distributed within the edge ring in predefined locations.

The void may have one of multiple geometric shapes, as discussed in more detail below. When the capping element 202 over the void is eroded due to exposure to plasma, the geometric shape of the void, all or part of it, will be visible and detectable through visual inspection.

Over time, capping element 202 gets eroded due to the operation of the chamber, at the same time that the edge ring 106 is eroded. Since the capping element 202 is coplanar with the top surface of the edge ring, the edge ring and the capping element will erode at the same rate because they are both formed of the same material. If the capping element were of a different material, there could be a process shift in the chamber due to the pollution in the chamber of the different material from the capping element.

When the capping element 202 is completely eroded, the space 204 appears visible on the surface of edge ring 106, and visual inspection can identify the hole to determine the lifetime of edge ring 106.

The appearance of the hole on the surface of the edge ring 106 may indicate that the edge ring should be replaced right away, or that the edge ring should be scheduled for replacement within a predetermined number of hours of operation of the chamber. For example, the replacement may be scheduled for 24 hours, or a different number of hours, or for a predetermined number of days or weeks, or a predetermined number of wafers processed, or a predetermined number of batches processed, or a predetermined number of lots processed, etc. This allows the operator of the semiconductor manufacturing equipment to plan proper maintenance for the edge ring, replacing the edge ring before performance of the equipment deteriorates.

It is noted that embodiments presented herein are described with reference to edge rings, but the principles may be equally applied to other consumable parts that suffer erosion or degradation over time, such as confinement rings, wall covers, liners, shower heads, focus rings, shrouds, etc.

Figure 2B:
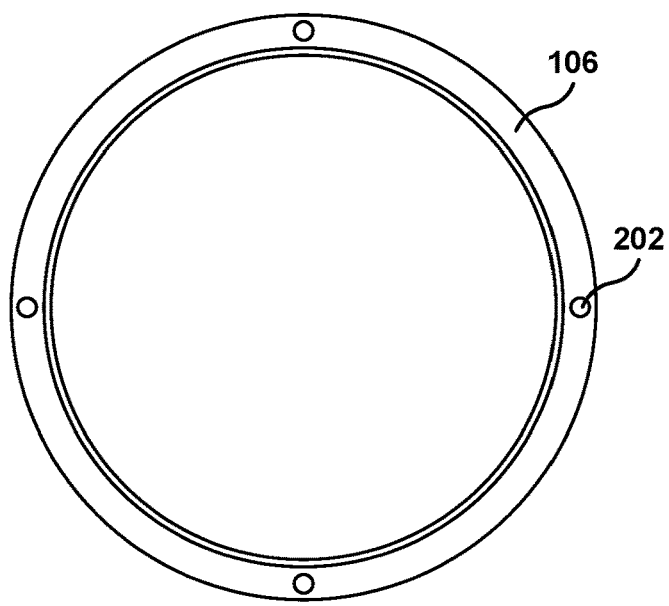
FIG. 2B is a top view of an edge ring with multiple trigger features, according to one embodiment.

FIG. 2B is a top view of an edge ring with multiple trigger features, according to one embodiment. The trigger feature may be installed on the edge ring 106 one or more times. For example, in one embodiment, the trigger feature is placed once in the edge ring 106 (not shown). In the exemplary embodiment of FIG. 2B, four trigger features 202 have been distributed over the surface of edge ring 106. This way, an inspection of about 90° of the surface of the edge ring 106 is enough to determine if the trigger feature has been activated. Also, by distributing the trigger features along the surface of the edge ring, it is possible to determine if there is uneven wear on the surface of the edge ring.

In some embodiments, the trigger feature is set to have been activated when the capping element of the trigger feature has been eroded, leaving the space below uncovered. In other embodiments, the trigger feature is said to have been activated based on the visible amount of hole surface.

The embodiment shown in FIG. 2B shows that the diameter of the capping feature occupies about half or more of the width of the edge ring. In other embodiments, the capping element may occupy from 10% to 50% of the width of the edge ring. In other embodiments, the diameter of the capping element may occupied from 50% to 90% of the width of the edge ring.

It is noted, that the shape of the capping element is a circular in the embodiment of FIG. 2B, but other embodiments may include capping elements with different shapes, as described in more detail below with reference to FIGS. 4A-4D and 5A-5F.

In one embodiment, the depth of the trigger feature (including both capping element 202 and micro chamber 204) is about one half of the width of the edge ring 106. In other embodiments, the depth of the trigger feature may be in the range from 10% to 90% of the width of the edge ring 106. In some embodiments, the depth of the trigger feature may be even 100%, or close to 100%, of the width of the edge ring, as described below with reference to FIGS. 6G and 6H.

Figure 3A:
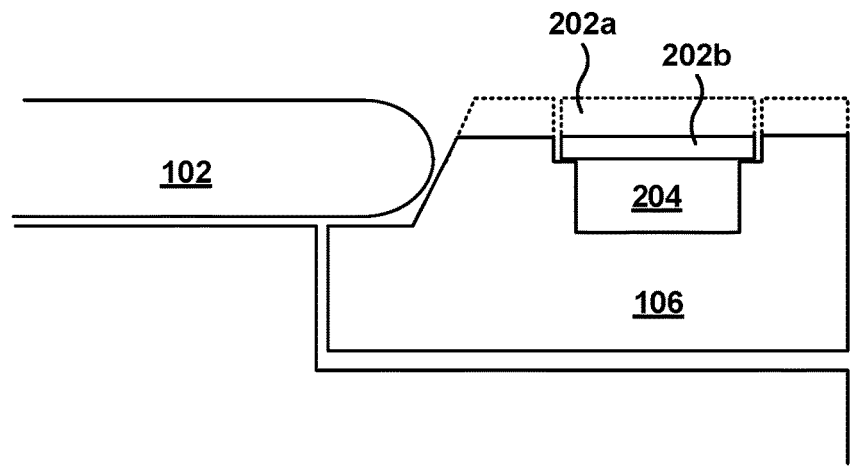
FIG. 3A illustrates an edge ring with erosion on the top surface, according to one embodiment.

FIG. 3A illustrates an edge ring with erosion on the top surface, according to one embodiment. Over time, the edge ring 106 and capping element 202 are reduced in width due to the etching of their surfaces when operating the chamber.

In FIG. 3A, there has been erosion on the surface of the edge ring and the capping element. A portion 202a of the capping element has been destroyed, while portion 202b still remains above the vacuum micro chamber 204. Therefore, at this point, micro chamber 204 has not been exposed yet and the trigger is not visible by visual inspection.

Figure 3B:
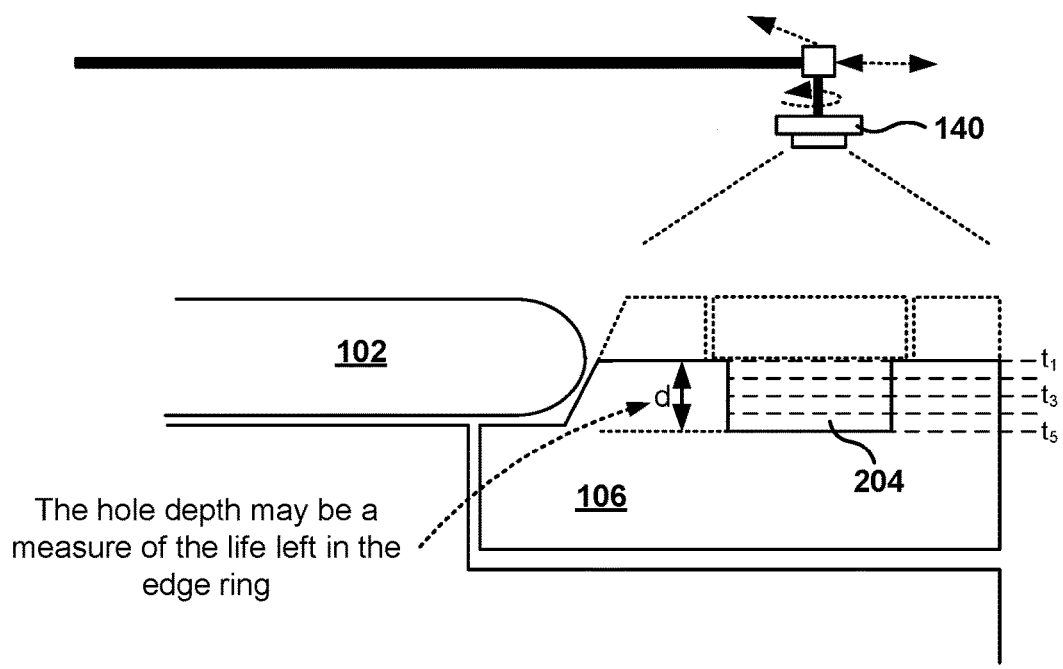
FIG. 3B illustrates the edge ring when the trigger cap has been completely eroded.

FIG. 3B illustrates the edge ring when the trigger cap has been completely eroded, according to one embodiment. The trigger feature enables detection of the end of life edge ring 106. At this point, the capping element has been completely destroyed, and the hole of chamber 204 is visible by visual inspection. For example, a borescope 140 can be introduced in the chamber to take images of the edge ring, and the images are then analyzed for detecting presence of the hole. The borescope may utilize images of the visible spectrum, infrared images, sound waves, ultrasound waves, or radiofrequency waves to detect the hole on the edge ring.

In one embodiment, the analysis of the images taken with the borescope 140 includes determining the depth remaining of micro chamber 204. Then, an estimate is made on the lifetime left on the edge ring based on the depth. For example, a first depth may indicate that the edge ring should be replaced after a period $t_1$, while another depth indicates replacement after a period $t_3$, etc. In another embodiment, the appearance of the hole on the surface of the edge ring is an indication that the edge ring should be replaced immediately, as soon as possible, or within a predetermined amount of time as indicated by the controller.

In one embodiment, the controller sets the predetermined amount of time left for the edge ring after detecting the hole for the first time. For example, the controller may set up a fix predetermined amount of time left on the edge ring, or the controller may set up on amount of time left on the edge ring depending on the process being used in the chamber. For example, testing may be performed while operating the chamber for different processes, and then an amount of time determined for each process based on the first time that the hole is detected.

Therefore, the edge ring has been modified with the trigger feature, such that when end of life is reached, a mark appears that can be detected by simple, automated optical inspection and image processing. The inspection of the trigger feature may be performed, for example, during lot changes (e.g., before loading a group of wafers into the semiconductor manufacturing equipment), with no impact to the throughput, and with a small impact on the cost of operating the equipment. By optimizing consumable-part lifetime, the cost of consumable-parts goes down and the performance of the semiconductor manufacturing equipment improves.

Figure 4A:
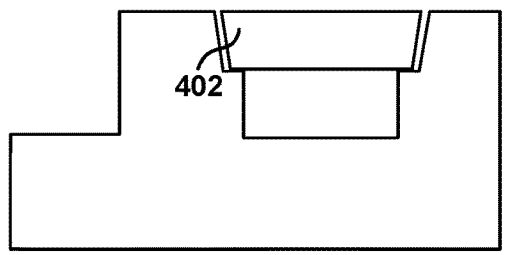
FIGS. 4A-4C illustrate several embodiments of trigger features that can be embedded in an edge ring.
Figure 4B:
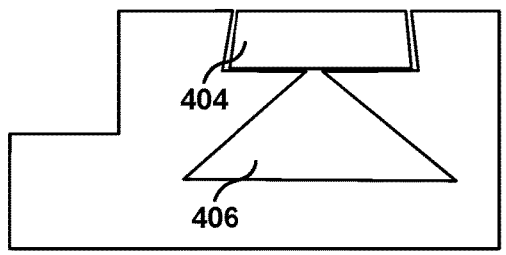
Figure 4C:
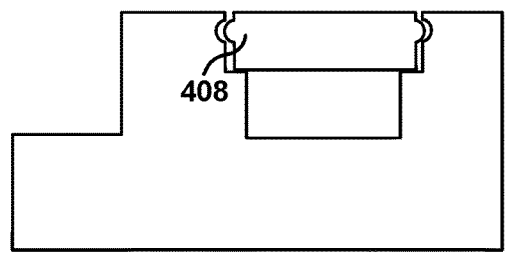

FIGS. 4A-4C illustrate several embodiments of trigger features that can be embedded in an edge ring. FIG. 4A illustrates a capping element 402 that has the shape of an inverted truncated cone. During manufacturing, the capping element 402 may be glued to the edge ring, or attached by having a side surface that interlocks with the corresponding surface of the edge ring.

FIG. 4B illustrates a capping element 404 which has the shape of a truncated cone. During manufacturing of the edge ring, capping element 404 is pushed into the cavity and the capping element 404 stays in place due to the wider circumference at the bottom than at the top. In another embodiment, capping element 404 is a truncated pyramid.

Additionally, in some embodiments, the vacuum micro chamber 406 has the shape of a pyramid, or a truncated pyramid, or a cone, or a truncated cone. This way, once the capping element is destroyed, the visible area of the hole grows over time, indicating how much lifetime is left in the edge ring.

In the embodiment of FIG. 4C, capping element 408 includes a protrusion ring defined to fit in a corresponding indention of the edge ring. During manufacturing of the edge ring, capping element 408 is pushed into the edge ring, until the protrusion locks the capping element in place. Other embodiments might have other interlocking mechanisms, such as interlocking mechanisms in the shape of saw teeth.

Figure 4D:
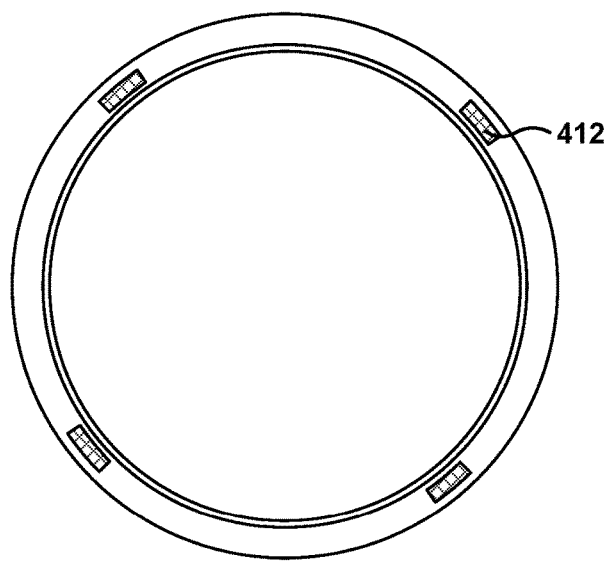
FIG. 4D is a top view of an edge ring with trenched trigger features, according to one embodiment.

FIG. 4D is a top view of an edge ring with trenched trigger features, according to one embodiment. As discussed above, the capping element may be circular on the top, but other shapes are also possible. For example, in the exemplary embodiment of FIG. 4D, the trigger feature has the shape of a trench that runs along the top of the edge ring.

The length of the trench may vary from one or more millimeters up to covering most, or all, of the circumference of the edge ring. Additionally, there could be one or more trenches spread out throughout the surface of the edge ring. For example, the number of triggering features on the edge ring may vary from one to 100 or more. In addition, the depth of the trigger features may be the same for all trigger features, or may vary for some of the trigger features, as discussed in more detail below.

FIG. 5A is a top view of a trigger feature having three holes of different lengths, according to one embodiment. In this embodiment, the trigger features have a top surface, where two sides (corresponding to a radial direction of the edge ring) are straight lines, while the other two sides that run concentrically with the edge ring are arcs with center on the center of the edge ring.

In the exemplary embodiment of FIG. 5A, three triggers are embedded into the edge ring. FIG. 5B shows a side view of the edge ring from FIG. 5A. Each of the trigger features has a different depth, therefore, as etching of the edge ring takes place, the number of visible holes 502, 504, 506, will start with 0, then go to 3 (assuming uniformity in the etching) when all caps are worn off. As erosion continues, one hole will disappear, and the number of holes will be 2, etc. The number of visible holes is then used as a metric to determine the consumable-part lifetime left.

FIGS. 5C-5F illustrate the top views of trigger features with different configurations, according to several embodiments. FIG. 5A shows a trigger feature 508 having a zigzag shape, similar to a thread on a car tire. In another embodiment, (not shown) the trigger feature has a curved zigzag shape, similar to a snake slithering across a field.

FIG. 5D includes two trenches 510 running in parallel on the surface of the edge ring. This improves the detectability of the trigger feature via image analysis.

FIG. 5E illustrates a plurality of trigger features 512 defined over the surface of the edge ring. For example, in one embodiment, the edge ring includes six trigger features, disposed in a 3×2 configuration over the surface of the edge ring. FIG. 5F illustrates a trigger feature 514 that has a triangular top surface.

FIGS. 6A-6H illustrate a plurality of different trigger features having different shapes, according to several embodiments. In some embodiments, the trigger feature does not include a capping element, and the spaces are visible from the time the edge ring is manufactured. Further, it is noted that other embodiments may have the same trigger features as those in FIGS. 6A-6F but with the addition of one or more capping elements. In some embodiments, there could be a combination of holes in the edge ring with and without caps.

Figure 6A:
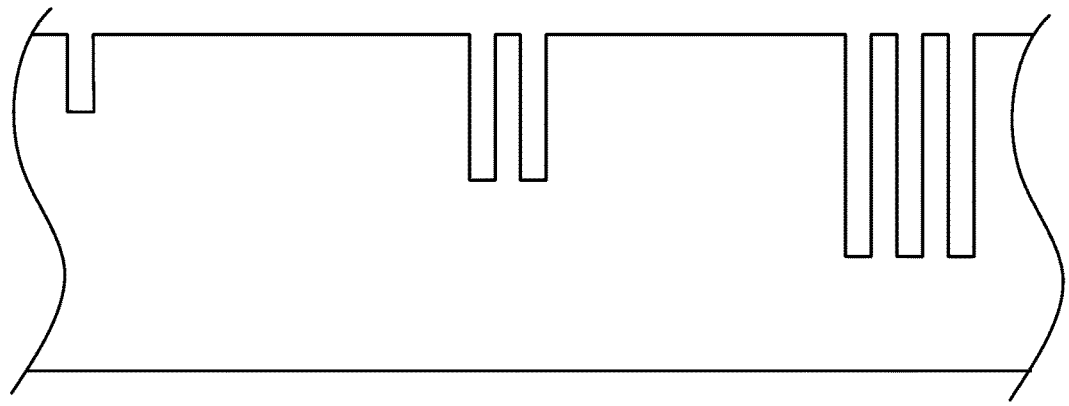
FIGS. 6A-6H illustrate a plurality of different trigger features having different shapes, according to several embodiments.

FIG. 6A includes six spaces in the edge ring, where one space has a first depth, two spaces have a second depth greater than the first depth, and three spaces have a third depth greater than the second depth. In one embodiment, the spaces are spaced apart to avoid the appearance of a feature with holes bunched together, and which appears as a big hole to the plasma, resulting in a process shift in the chamber. In order to avoid the process shift, the holes are spaced apart to avoid creating a lack of uniformity over the surface of the edge ring.

Initially, visual inspection will show 6 spaces, and over time, the first space will disappear, leaving 5 spaces visible. Later, 3 spaces will be visible when more surface of the ring is etched away. If the holes are capped, then the features could be closer together because the holes would not be facing the plasma.

Figure 6B:
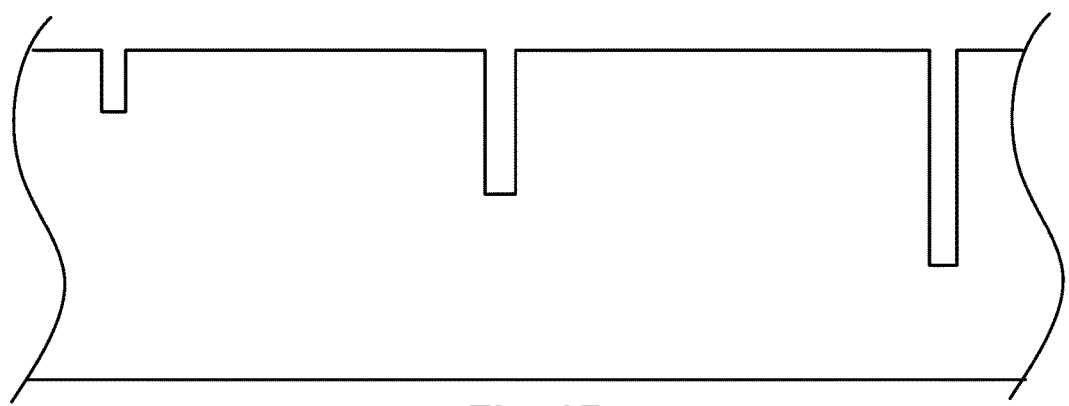

Similarly to FIG. 6A, FIG. 6B includes three features with different depths. The lifetime of the edge ring will be measured by the amount of visible holes, and/or the depth of the visible holes.

Figure 6C:
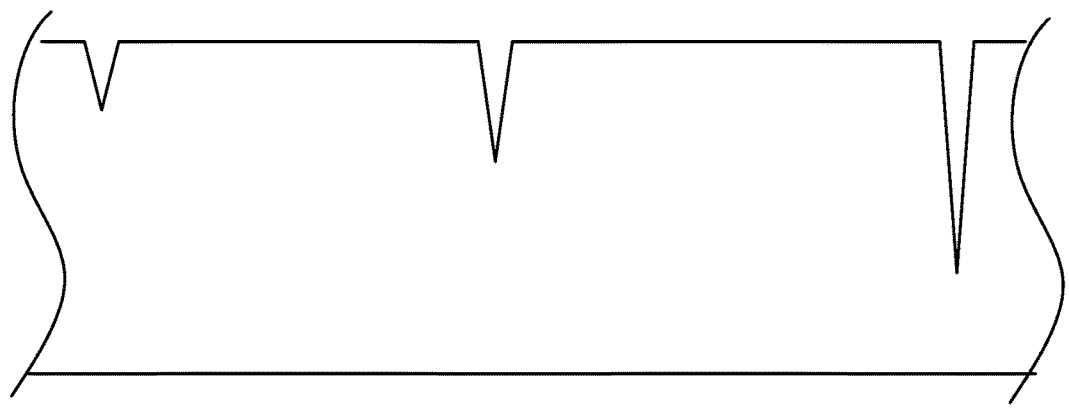

FIG. 6C illustrates three triggering features with inverted conical shapes, and with different depths. In another embodiment, the shapes of the holes are inverted pyramids. As before, the number of visible holes will determine the lifetime of the part, and the size of the holes will also provide an indication of how deep the holes are, because as the holes become less deep (e.g., the surface of the ring is etched) the sizes of the holes decrease.

Additionally, the size of each hole is configured to avoid creating a process shift in the chamber when the hole becomes visible. If the hole is too big, the plasma could enter the hole and create a lack of uniformity over the surface of the edge ring. In addition, the holes are spaced apart to avoid process shift when the holes become visible. If several holes are close together, they may behave to the plasma as one big hole, thereby creating a lack of uniformity and a process shift in the chamber. To avoid the process shift, the holes are configured to be spaced apart, so when the holes become visible to the plasma, the holes do not cause a process shift.

Figure 6D:
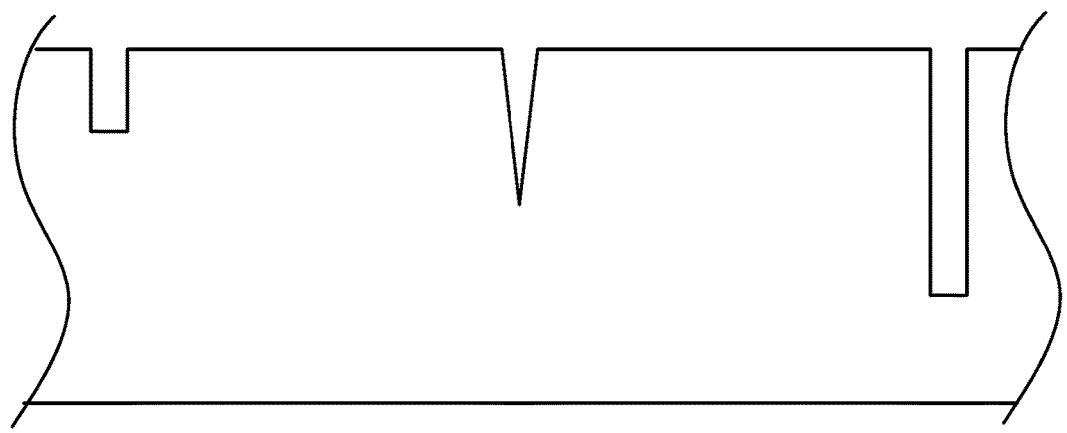

FIG. 6D illustrates trigger features that have different shapes. For example, a first feature has a short depth and a rectangular cross-section, a second feature is deeper than the first feature and has a conical shape, and the third feature is deeper than the other two features and has a rectangular cross-section. By providing different depths and feature shapes, the image analysis of the surface of the ring will provide more information on the lifetime left on the ring, based on the number of visible holes, and the size of the holes.

Figure 6E:
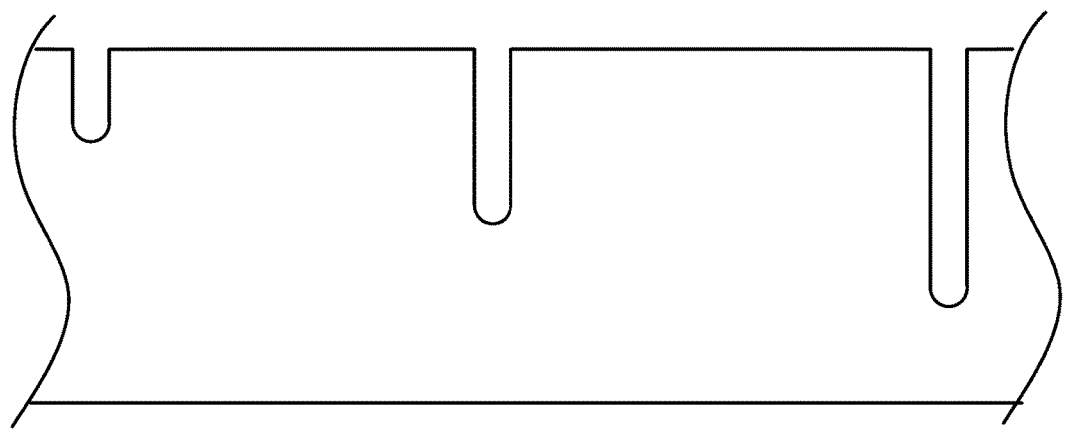

FIG. 6E illustrates an embodiment that includes three triggering features having three different depths and spherical bottoms, similar to test tubes of different sizes.

Figure 6F:
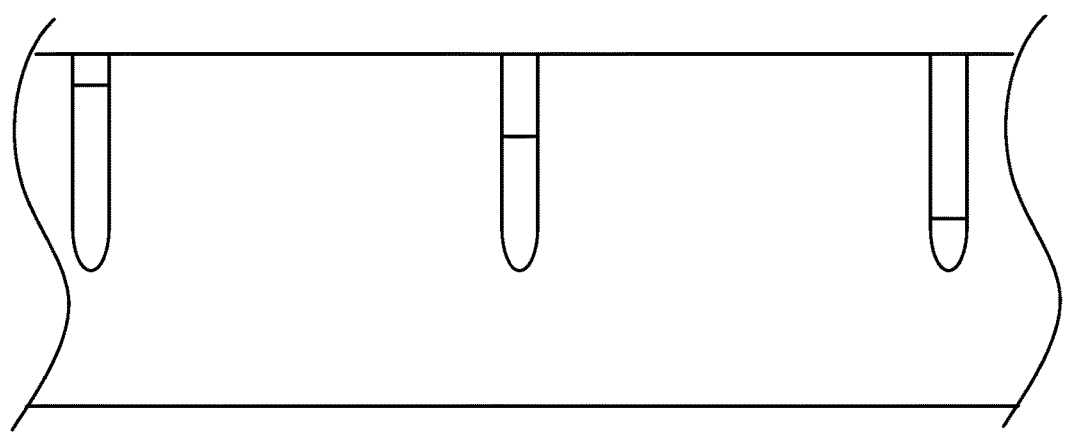

FIG. 6F illustrates an embodiment of three triggering features with the same depth and spherical bottoms. Additionally, the embodiment of FIG. 6F includes caps of different heights. As a result, as erosion takes place, a first hole will be visible first, then when erosion continues, a second hole will also be visible, and eventually all three holes will be visible when erosion edges all 3 capping elements. The number of visible holes can then be used as a measure of the lifetime remaining for the edge ring.

Figure 6G:
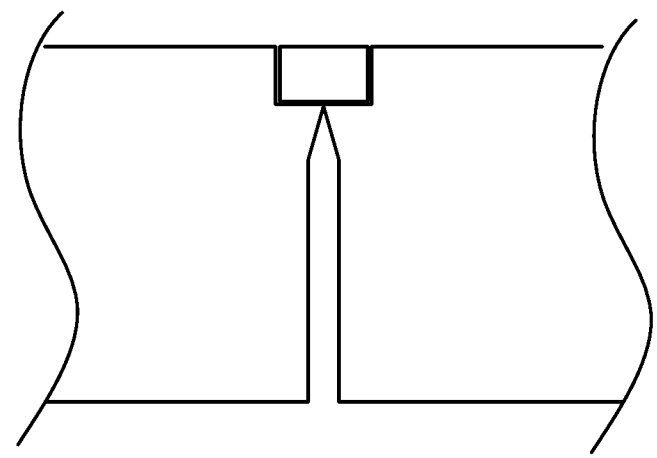
Figure 6H:
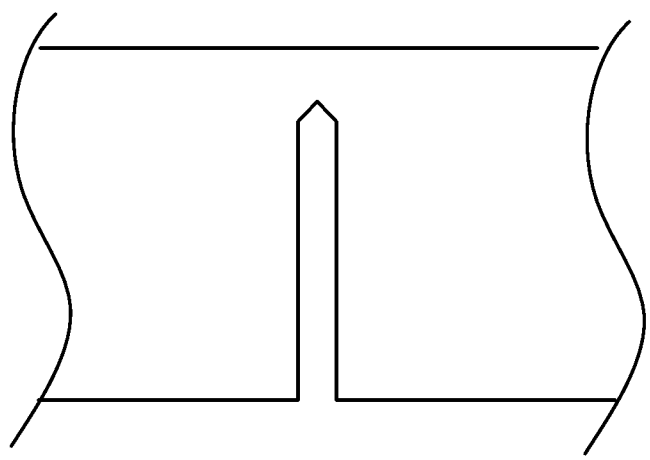

FIGS. 6G and 6H show edge rings where the trigger feature does not have a bottom surface, i.e., the trigger feature is defined to reach the bottom of the edge ring. FIG. 6G illustrates a trigger feature that has a capping feature extending from the top surface of the edge ring, and a hollow space below the capping feature that reaches the bottom of the edge ring. In one embodiment, the shape of the hollow space is conical or pyramidal, although other shapes are also possible. In operation, the surface of the edge ring will be initially flat, but after the capping feature is etched away, a hole will appear in the surface of the edge ring. As etching continues and more of the edge ring surface is etched away, the size of the hole will grow, thereby providing an indication of the lifetime left of the consumable part.

FIG. 6H is similar to FIG. 6G, but there is no capping element, because the space is covered by the edge ring itself. One of the advantages of the embodiment of FIG. 6H is that the trigger feature is a notch at the bottom of the edge ring and is easy to manufacture because all it requires is to change the shape of the edge ring.

It is noted that the embodiments illustrated in the Figures described above are exemplary. Other embodiments may utilize different combinations of the features previously described, e.g., change in the number of trigger features, the distribution of the trigger features over the surface of the edge ring, the size and shape of the capping element, the size and shape of the space below the capping element, etc. The embodiments illustrated in FIGS. 1A-1B, 2A-2B, 3A-3B, 4A-4E, 5A-5F, and 6A-6H should therefore not be interpreted to be exclusive or limiting, but rather exemplary or illustrative.

Figure 7A:
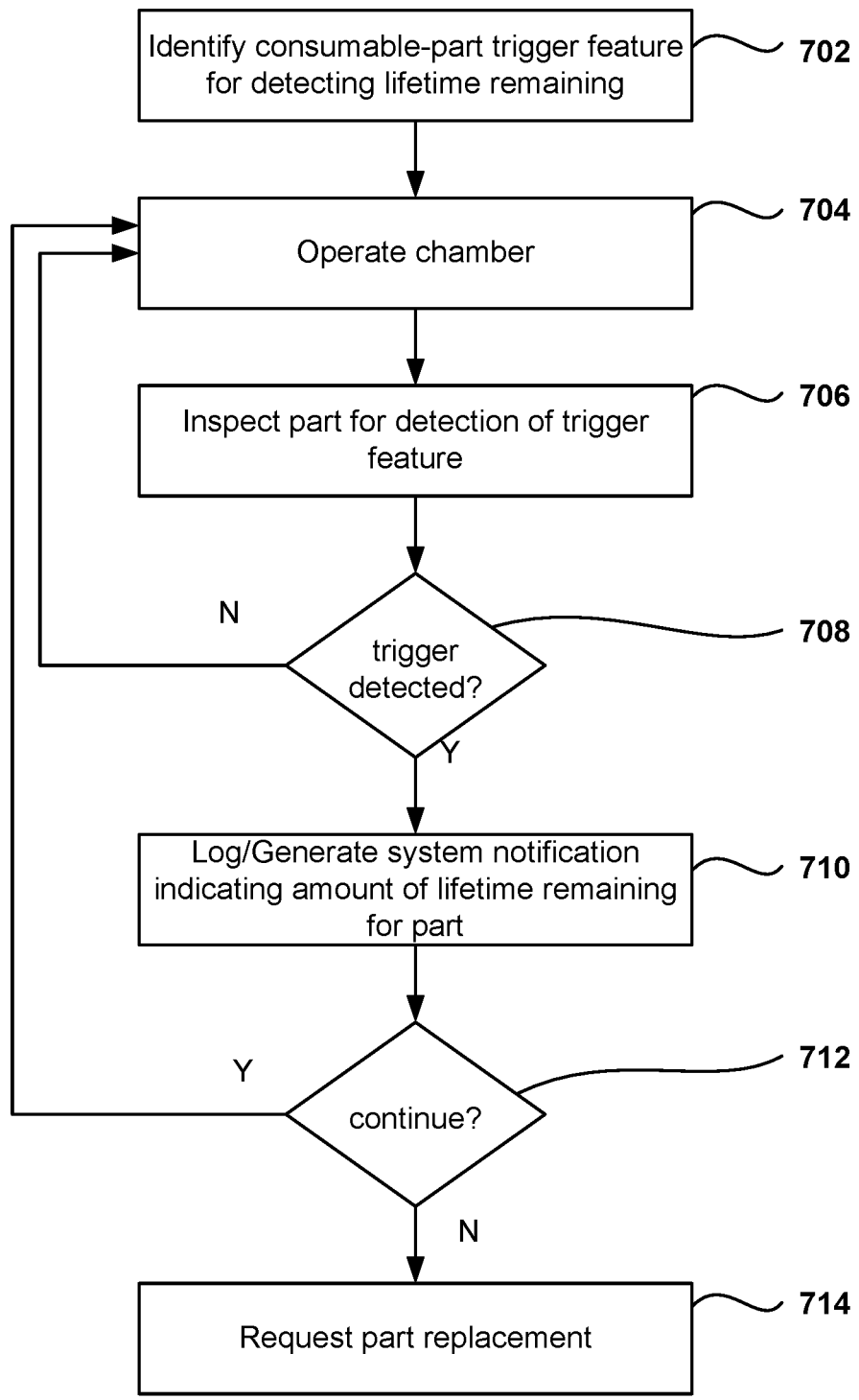
FIG. 7A is a flowchart of a method for determining if a consumable part needs replacement, according to one embodiment.

FIG. 7A is a flowchart of a method for determining if a consumable part needs replacement, according to one embodiment. While the various operations in this flowchart are presented and described sequentially, one of ordinary skill will appreciate that some or all of the operations may be executed in a different order, be combined or omitted, or be executed in parallel.

In operation 702, a trigger feature of our consumable part is identified for detecting the lifetime remaining of the consumable part. For example, the trigger feature may be the trigger feature 202 of FIG. 2A, and the lifetime of the edge ring is considered extinguished when the vacuum microchamber 204 is exposed and visible on the surface of the edge ring. In another embodiments, the edge ring is considered to have a predetermined amount of lifetime left the first time that the trigger feature is visible on the surface of the edge ring. Other embodiments may include different type of triggers and different ways of measuring the lifetime remaining of the consumable part based on the changes in the shape or size of the trigger features.

From operation 702, the method flows to operation 704 where the chamber in the semiconductor manufacturing equipment is in operation. From operation 704, the method flows to operation 706 where a consumable part is inspected for a possible detection of a trigger feature that indicates lifetime remaining on the consumable part.

From operation 706, the method flows to operation 708 where a check is made to determine if the trigger was detected in operation 706. If the trigger was detected, the method flows to operation 710, and if the trigger was not detected the method flows to operation 704 to continue operation of the chamber.

In operation 710, the detection of the trigger is logged and/or a system notification is generated, the system notification indicating the amount of lifetime remaining for the consumable part. In one embodiment, historical measurements, for the performance of a consumable part based on the trigger detected, are used for predicting the lifetime left in the consumable part.

From operation 710, the method flows to operation 712 where a check is made to determine if operation of the chamber can continue. For example, if the trigger feature detects that performance of the chamber will be below an unacceptable threshold, the system may determine that operation of the chamber cannot continue until the consumable part is replaced. If it is possible to continue, the method flows back to operation 704 to operate the chamber, and if it is determined that the chamber operation cannot continue, the method flows to operation 714 where a consumable-part replacement is requested.

It is noted that this method may be applied to any part that can be inspected by the borescope, which can be injected from a side of a small gate valve (as seen in FIG. 1A). By performing the inspection while the chamber is not operating, it is possible to avoid the contamination of the borescope and/or the wafer during processing.

Figure 7B:
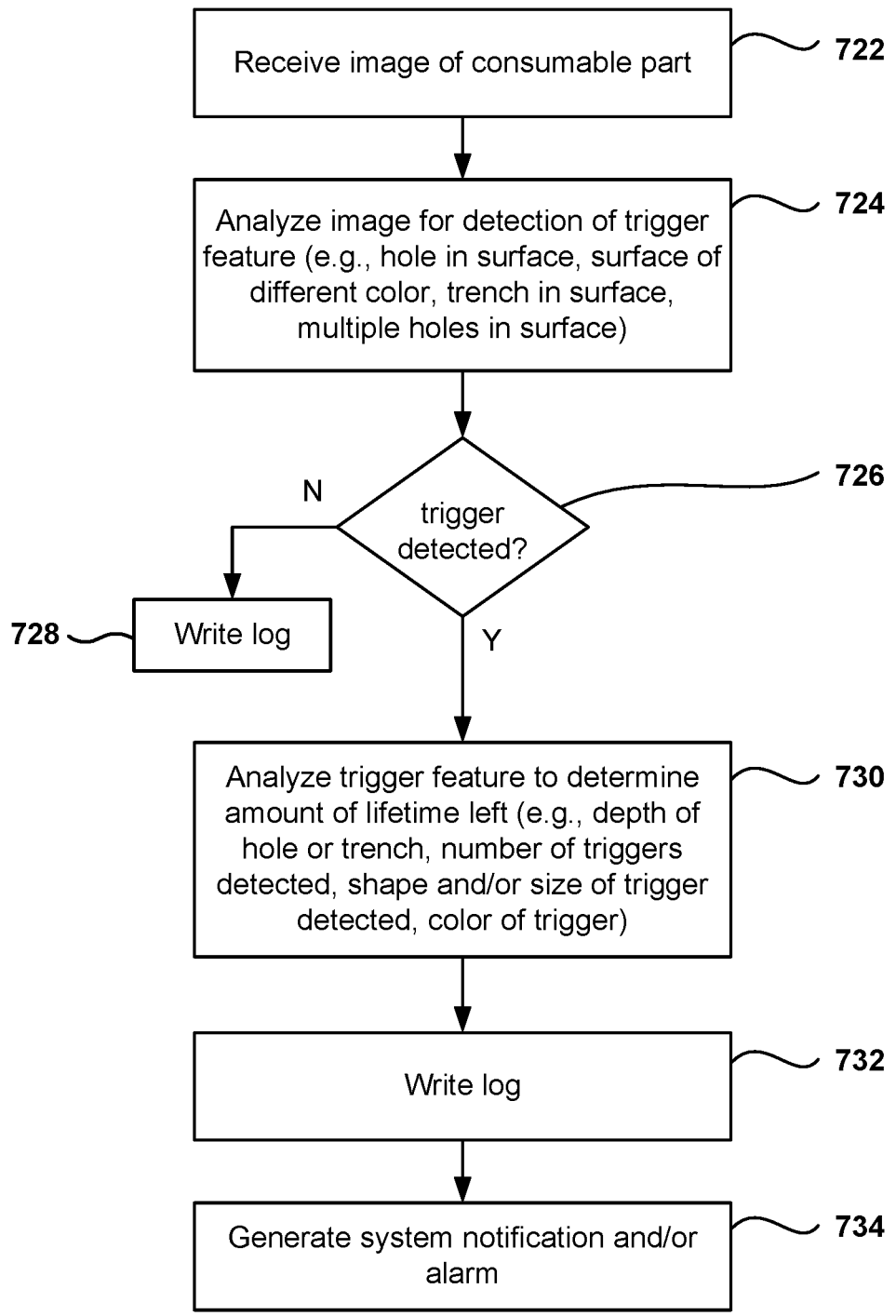
FIG. 7B is a flowchart of a method for determining the lifetime remaining of a consumable part, according to one embodiment.

FIG. 7B is a flowchart of a method for determining the lifetime remaining of a consumable part, according to one embodiment. While the various operations in this flowchart are presented and described sequentially, one of ordinary skill will appreciate that some or all of the operations may be executed in a different order, be combined or omitted, or be executed in parallel.

In operation 722, an image (or images) is received by an image analyzer in communication with the system controller. The received image is of a consumable part of a semiconductor manufacturing system.

From operation 722, the method flows to operation 724 where the received image (or images) is analyzed for the detection of a trigger feature that may indicate a condition related to the lifetime of a consumable part, such as an indication that the consumable part must be replaced, or that it must be replaced within a predetermined amount of time. The trigger feature detection may include the detection of one or more of a hole in a surface of the consumable part, an area in the surface of a different color from the overall area of the consumable part, the appearance of a trench on the surface of the consumable part, the appearance of one or more holes on the surface of the consumable part, etc.

From operation 724, the method flows to operation 726 where a check is made to determine if the trigger was detected in operation 724. If the trigger was detected, the method flows to operation 730, and if the trigger was not detected, the method flows to operation 728, where a log entry is written indicating that the analysis was performed and the trigger was not detected.

The trigger feature, in one embodiment, may be any feature that will show an abrupt change in the optical image that makes detection fast and un-ambiguous. In one embodiment, differences in materials or gross changes in geometry are avoided, as they may create problems of contamination and/or process shift.

In operation 730, the trigger feature is analyzed to determine an amount of lifetime left for the consumable part, or if the consumable part has no lifetime left. The analysis may be based on the depth of a hole or trench, a shape of the visible hole on the surface of the consumable part, the number of trigger features detected on the surface of the consumable part, the safe and/or size of the trigger detected, an area on the consumable part with a different color from the color of the consumable part, etc.

From operation 730, the method flows to operation 732 where a log entry is created indicating the results of the analysis. From operation 732, the method flows to operation 734 where a system notification is generated for the system administrator of the semiconductor manufacturing equipment, and/or an alarm is generated indicating that the consumable part must be replaced immediately, or within a predetermined amount of time.

Figure 7C:
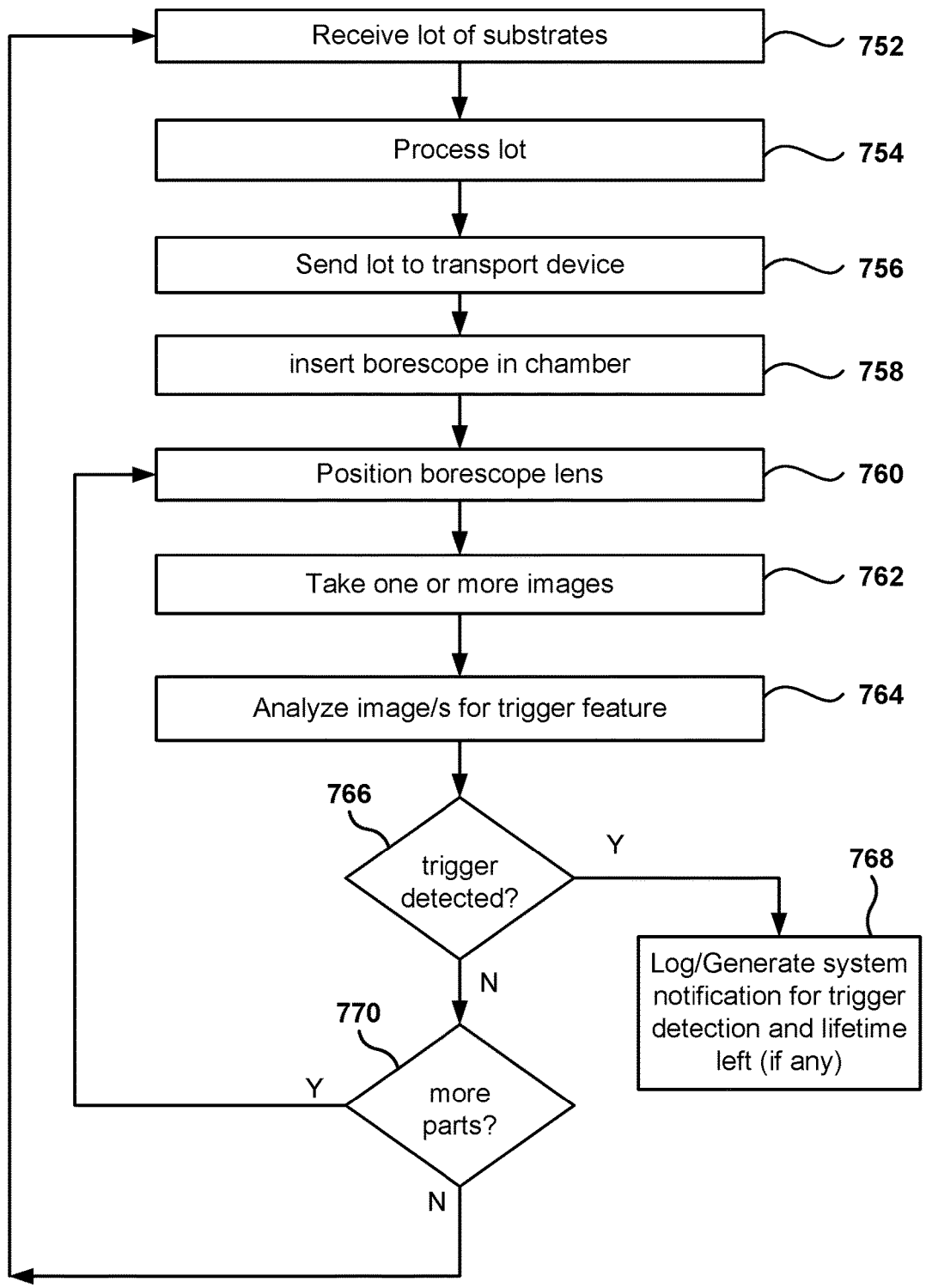
FIG. 7C is a flowchart of a method for scheduling inspection of consumable parts during the operation of a semiconductor processing chamber, according to one embodiment.

FIG. 7C is a flowchart of a method for scheduling inspection of consumable parts during the operation of a semiconductor processing chamber, according to one embodiment. In operation 752, a semiconductor manufacturing machine receives a lot of substrates, which includes a plurality of substrates to be processed. In one embodiment, the process includes etching of the features on the surface of the substrates.

During operation 754, the lot of substrates is processed by the semiconductor manufacturing equipment. From operation 754, the method flows to operation 756, when the lot exits the manufacturing equipment and is sent to a transport device.

After the lot has been processed, in operation 758, a borescope is inserted in the chamber while the chamber is not in operation. Once the borescope is injected into the chamber, the borescope can be rotated 760 and translated to inspect various parts inside the chamber. In operation 762, the borescope takes one or more images of a consumable part to be inspected.

In operation 764, the image or images taken by the borescope are analyzed for a possible detection of one or more trigger features. Each image can be processed to detect change in morphology indicating if wear lifetime has been reached. The detection of a defective edge ring is critical for applications where the wear of the edge ring may cause a process shift or drift.

From operation 764, the method flows to operation 766 where a check is made to determine if the trigger has been detected. If the trigger has been detected, the method flows to operation 768, and if the trigger has not been detected, the method flows to operation 770.

In operation 768, an entry is made in the system log indicating that the trigger has been detected. In addition, the system may generate one or more system notifications based on the trigger detection, and identify how much lifetime is left on the consumable part, or if there is no lifetime left in the consumable part.

In operation 770, a check is made to determine if the borescope is needed to analyze additional consumable parts. If more parts are to be examined, the method flows back to operation 760 to position the borescope for taking images, and if no more parts are to be inspected, the method flows back to operation 752, where the system is ready to receive a new lot of substrates.

In one embodiment, a method for detecting wear on an edge ring includes an operation for placing the edge ring in a semiconductor manufacturing chamber. The edge ring is configured to surround a substrate during processing, and the edge ring includes an annular body and a trigger feature within the annular body. The trigger feature includes a capping element covering a hole, and the hole is visible when the capping element is eroded.

The method further includes operations for inserting an inspection scope in the chamber, and for analyzing images of the edge ring captured by the inspection scope to determine if the capping element is visible. Further, the method includes an operation for determining an amount of time left before replacing the edge ring in the chamber when the hole is visible.

Embodiments presented herein provide methods, systems, and computer programs for predicting time for wet clean, resulting in increased manufacturing predictability, while downtime is minimized. By managing consumable-part lifetime, the cost of the consumable parts is minimized while the operation of the chamber is improved.

In one embodiment, the trigger feature is designed such that a lifetime clock is associated with the trigger feature. The operator of the equipment is able to define when to clean or replace a part based on the information provided by the trigger feature on the corresponding analysis by the image analyzer.

Figure 8:
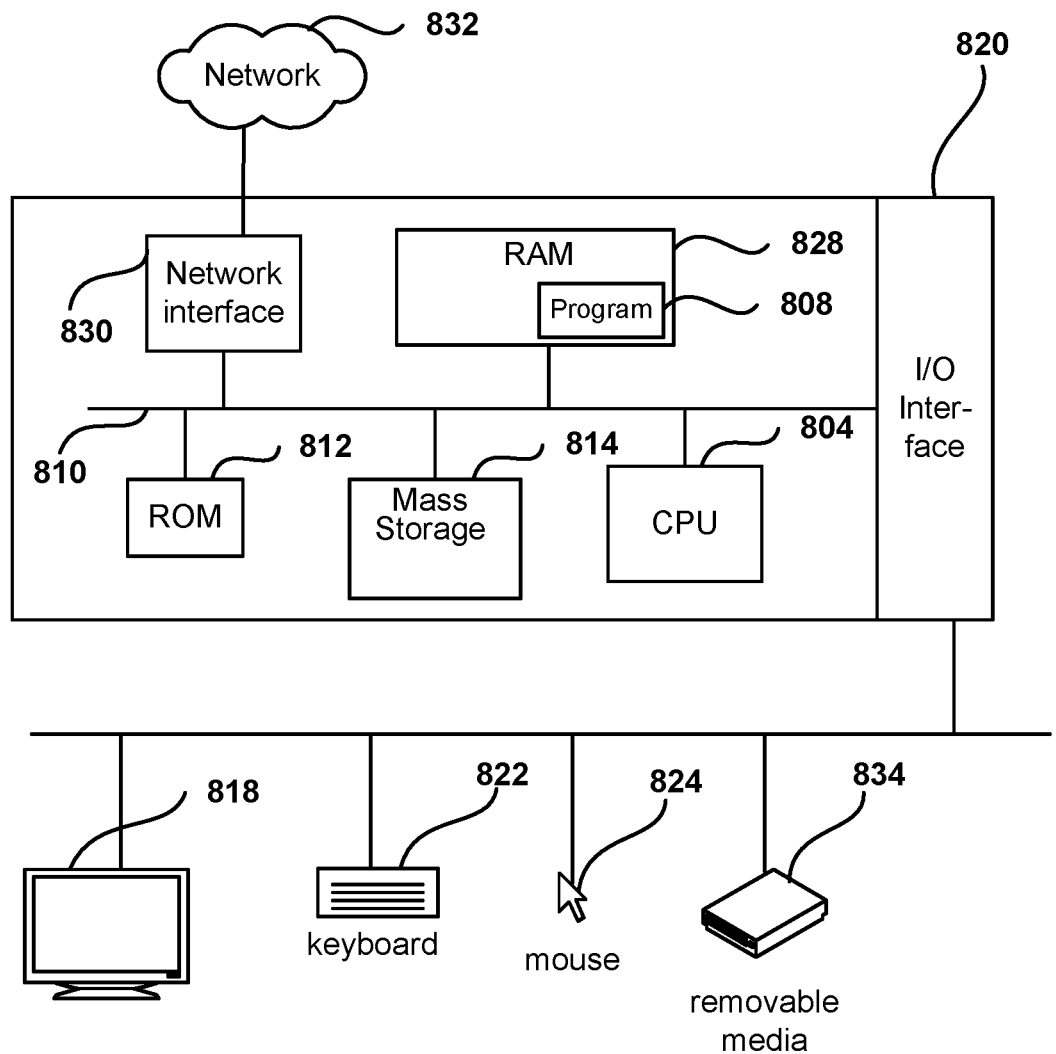
FIG. 8 is a simplified schematic diagram of a computer system for implementing embodiments of the present invention.

FIG. 8 is a simplified schematic diagram of a computer system for implementing embodiments. It should be appreciated that the methods described herein may be performed with a digital processing system, such as a conventional, general-purpose computer system. Special purpose computers, which are designed or programmed to perform only one function may be used in the alternative. The computer system includes a central processing unit (CPU) 804, which is coupled through bus 810 to random access memory (RAM) 806, read-only memory (ROM) 812, and mass storage device 814. System controller program 808 resides in random access memory (RAM) 806, but can also reside in mass storage 814.

Mass storage device 814 represents a persistent data storage device such as a floppy disc drive or a fixed disc drive, which may be local or remote. Network interface 830 provides connections via network 832, allowing communications with other devices. It should be appreciated that CPU 804 may be embodied in a general-purpose processor, a special purpose processor, or a specially programmed logic device. Input/Output (I/O) interface provides communication with different peripherals and is connected with CPU 804, RAM 806, ROM 812, and mass storage device 814, through bus 810. Sample peripherals include display 818, keyboard 822, cursor control 824, removable media device 834, etc.

Display 818 is configured to display the user interfaces described herein. Keyboard 822, cursor control 824, removable media device 834, and other peripherals are coupled to I/O interface 820 in order to communicate information in command selections to CPU 804. It should be appreciated that data to and from external devices may be communicated through I/O interface 820. The embodiments can also be practiced in distributed computing environments where tasks are performed by remote processing devices that are linked through a wire-based or wireless network.

Embodiments may be practiced with various computer system configurations including hand-held devices, microprocessor systems, microprocessor-based or programmable consumer electronics, minicomputers, mainframe computers and the like. The embodiments can also be practiced in distributed computing environments where tasks are performed by remote processing devices that are linked through a network.

With the above embodiments in mind, it should be understood that the embodiments can employ various computer-implemented operations involving data stored in computer systems. These operations are those requiring physical manipulation of physical quantities. Any of the operations described herein that form part of the embodiments are useful machine operations. The embodiments also relates to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data may be processed by other computers on the network, e.g., a cloud of computing resources.

One or more embodiments can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the embodiments are not to be limited to the details given herein, but may be modified within the scope and equivalents of the appended claims.

The invention claimed is:

1. A consumable part for use inside a chamber where plasma is used to process a semiconductor substrate, the consumable part comprising:
    a body having a surface configured to be exposed to the plasma during processing in the chamber; and
    a trigger feature integrated within the body, the trigger feature including a void that is disposed under the surface of the body, wherein the void is configured to become visible when the surface is eroded from exposure to the plasma over time, the void becoming visible being an identifiable feature on the surface of the body that indicates a wear level for the consumable part, the wear level being associated with an amount of processing time remaining for the consumable part and the wear level is associated to an amount of the void that is visible and present from exposure to the plasma.

2. The consumable part as recited in claim 1, wherein the consumable part is associated with the amount of processing time remaining as correlated to a predetermined period a first time that the void having a predefined dimension is visible by an inspection scope.

3. The consumable part as recited in claim 1, wherein the trigger feature further includes a capping element that is substantially coplanar with a surface of the body, the capping element being situated above the void, the capping element being of a same material as the consumable part to avoid process shift in the chamber while processing the substrate.

4. The consumable part as recited in claim 1, wherein the consumable part further includes:
    one or more additional trigger features distributed over the consumable part.

5. The consumable part as recited in claim 4, wherein the one or more additional trigger features include capping elements of different depth.

6. The consumable part as recited in claim 4, wherein the one or more additional trigger features include respective voids of different depth.

7. The consumable part as recited in claim 1, wherein a capping element above the void is of a same material as the body.

8. A system comprising:
    a chamber configured for generating plasma used to process a semiconductor substrate;
    a consumable part for use inside the chamber, the consumable part including a body and a trigger feature, the body having a surface configured to be exposed to the plasma during processing in the chamber, the trigger feature being integrated within the body, wherein the trigger feature includes a void that is disposed under the surface of the body, wherein the void is configured to become visible when the surface is eroded from exposure to the plasma over time;
    an inspection scope for inspecting the consumable part while the consumable part is in the chamber; and
    a controller configured to determine if the void is visible based on information obtained by the inspection scope, the void becoming visible being an identifiable feature on the surface of the body that indicates a wear level for the consumable part, the wear level being associated with an amount of processing time remaining for the consumable part and the wear level is correlated to an amount that the void is visible to the inspection scope as the surface is eroded from exposure to the plasma over time, wherein a size of the void is configured to avoid process shift in the chamber when the void is exposed to the plasma after the surface is eroded.

9. The system as recited in claim 8, wherein the inspection scope is configured to inspect the consumable part utilizing one or more of images of the visible spectrum, infrared images, sound waves, ultrasound waves, and radiofrequency waves.

10. The system as recited in claim 8, wherein a depth of the trigger feature is about one half of a width of the body.

11. The system as recited in claim 8, wherein a depth of the trigger feature is in a range from 10% to 99% of a vertical width of the body.

12. The system as recited in claim 8, wherein a shape of the void is cylindrical.

13. The system as recited in claim 8, wherein a shape of the void is of a truncated cone.

14. The system as recited in claim 8, wherein the trigger feature further includes a capping element that is coplanar with a surface of the body, the capping element being situated above the void, wherein the capping element includes a protrusion ring configured to fit in a corresponding indention of the body.

15. A method for detecting wear on a consumable part, the method comprising:
    placing the consumable part in a chamber for semiconductor manufacturing, wherein the consumable part includes a body and a trigger feature, the body having a surface configured to be exposed to plasma during processing in the chamber, the trigger feature integrated within the body, wherein the trigger feature includes a void that is disposed under the surface of the body, wherein the void is configured to become visible when the surface is eroded from exposure to the plasma over time, the void becoming visible being an identifiable feature on the surface of the body that indicates a wear level for the consumable part;
    inserting an inspection scope in the chamber;

analyzing information obtained by the inspection scope to determine if the void is visible; and determining an amount of time left before replacing the consumable part in the chamber when the void is visible and the wear level is correlated to an amount that the void is visible using the inspection scope as the surface is eroded from exposure to the plasma over time.

16. The method as recited in claim 15, wherein the trigger feature further includes a capping element that is coplanar with a surface of the body, the capping element being situated above the void, wherein the capping element is circular.

17. The method as recited in claim 15, wherein a capping element above the void has a shape of a trench running along the body.

18. The method as recited in claim 15, wherein the trigger feature further includes one or more additional caps above corresponding additional voids.

19. The method as recited in claim 15, wherein the void has a shape of an inverted cone.

20. The method as recited in claim 15, wherein operations of the method are performed by a computer program when executed by one or more processors, the computer program being embedded in a non-transitory computer-readable storage medium.

* * * * *